United States Patent [19]
Silvian

[11] Patent Number: 5,350,405
[45] Date of Patent: Sep. 27, 1994

[54] METHOD AND APPARATUS FOR CAPACITOR TOLERANCE COMPENSATION IN A CARDIAC STIMULATING DEVICE

[75] Inventor: Sergiu Silvian, La Crescenta, Calif.

[73] Assignee: Siemens Pacesetter, Inc., Sylmar, Calif.

[21] Appl. No.: 946,276

[22] Filed: Sep. 16, 1992

[51] Int. Cl.$^5$ .............................................. A61N 1/08
[52] U.S. Cl. ........................................ 607/8; 607/11; 607/27; 607/7
[58] Field of Search .................... 607/8, 11, 27, 7, 12, 607/28, 29

[56] References Cited

U.S. PATENT DOCUMENTS

| | | | |
|---|---|---|---|
| 3,782,389 | 1/1974 | Bell | 607/8 |
| 4,606,350 | 8/1986 | Frost | 602/29 |
| 5,201,865 | 4/1993 | Kuehn | 607/8 |

*Primary Examiner*—William E. Kamm
*Assistant Examiner*—Kennedy J. Schaetzle
*Attorney, Agent, or Firm*—Malcolm J. Romano

[57] ABSTRACT

A method and apparatus for determining the actual capacitance of a capacitor in a cardiac stimulating device in order to determine the potential necessary to store a desired amount of energy on the capacitor, are provided. The discharge curve of the capacitor is measured during re-forming to determine the time constant of the capacitor and the dumping resistor, and hence the actual capacitance.

26 Claims, 2 Drawing Sheets

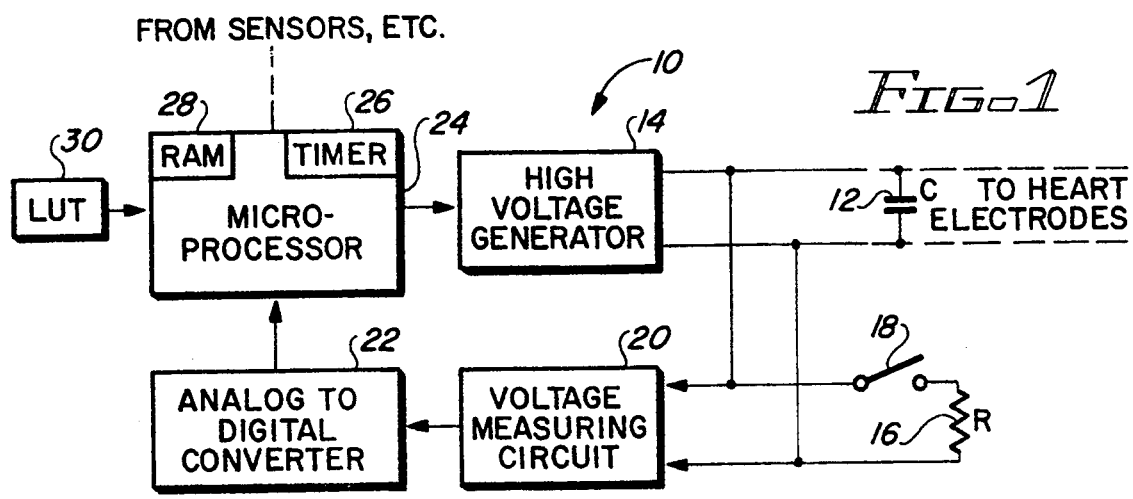
FIG-1
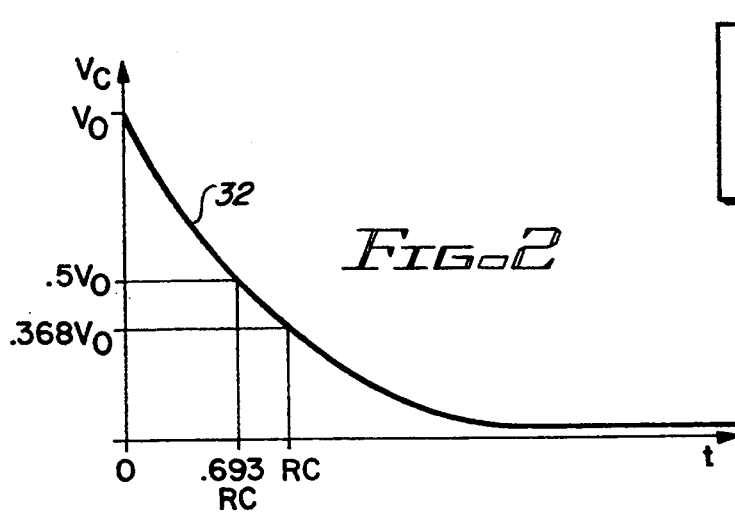
FIG-2
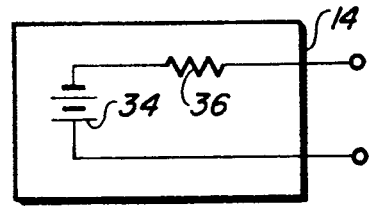
FIG-4
| E (JOULES) | TARGET POTENTIALS AT DETERMINED CAPACITANCE | | | | |
|---|---|---|---|---|---|
| | C=140μf | C=145μf | $C_{NOM}$=150μf | C=155μf | C=160μf |
| 40 | 756 | 743 | 730 | 718 | 707 |
| 35 | 707 | 695 | 683 | 672 | 661 |
| 30 | 655 | 643 | 632 | 622 | 612 |
| 25 | 598 | 587 | 577 | 568 | 559 |
| 20 | 535 | 525 | 516 | 508 | 500 |
| 15 | 463 | 455 | 447 | 440 | 433 |
| 10 | 378 | 371 | 365 | 359 | 354 |
| 5 | 267 | 263 | 258 | 254 | 250 |
FIG-3

METHOD AND APPARATUS FOR CAPACITOR TOLERANCE COMPENSATION IN A CARDIAC STIMULATING DEVICE

BACKGROUND OF THE INVENTION

This invention relates to cardiac stimulating devices and particularly to implantable cardiac stimulating devices, including implantable cardiac pacemakers and implantable cardiac defibrillators, as well as implantable cardioverters and cardioverter/defibrillators. More particularly, this invention relates to a method and apparatus for compensating for the tolerance in a capacitor in such a cardiac stimulating device.

An implantable cardiac stimulating device is designed to deliver electrical shocks, or "pulses," of varying energy content to the heart of a patient in whom it is implanted. The magnitude of the electrical pulse is relatively small in a pacemaker, relatively large in a defibrillator, and somewhere in between in a cardioverter. The magnitude of the electrical pulse to be delivered is calibrated in terms of energy, usually in joules. For example, a pacemaker might deliver a pulse on the order of about 25 μjoules to about 30 μjoules, while a defibrillator might deliver a pulse on the order of about 30 joules to about 40 joules.

The cardiac stimulating pulse is usually produced by discharging a capacitor in which the desired amount of energy has been stored. The amount energy E stored in a capacitor having a capacitance C is determined by the well known expression:

$$E = 0.5CV^2, \quad (1)$$

where V is the potential to which the capacitor is charged.

However, capacitors used in implantable cardiac stimulating devices may vary from their nominal capacitance. Indeed, the most commonly used capacitors in such devices are electrolytic capacitors, because of their higher capacitances. Such capacitors need periodic (e.g., every 3-4 months) "re-forming"—a full charge and discharge cycle—to maintain their capacitance. Electrolytic capacitors can initially vary from their nominal capacitances by as much as $+10\%/-20\%$, and their capacitance further changes with time. As a result, the stored energy can vary by as much as $\pm20\%$ from the calculated value, so that the pulse delivered to the patient may be either too small to have its desired clinical effect, or too large, wasting power.

In an implantable cardiac stimulating device, which ideally should not have to be replaced, it is desirable that appropriately sized pulses be delivered, both to achieve the desired clinical result in the patient and to avoid premature battery depletion which would necessitate early replacement. Therefore, accurate calibration of pulse energy is desirable.

It would be desirable to be able to determine the true capacitance of a capacitor in an implantable cardiac stimulating device, or to otherwise compensate for variations in capacitance.

It would also be desirable to be able to determine the capacitance, or to compensate for variations in capacitance, without having to provide additional components or using additional battery power.

SUMMARY OF THE INVENTION

It is an object of this invention to be able to determine the true capacitance of a capacitor in an implantable cardiac stimulating device, or to otherwise compensate for variations in capacitance.

It is also an object of this invention to be able to determine the capacitance, or to compensate for variations in capacitance, without having to provide additional components or using additional battery power.

In accordance with this invention, there is provided a method for determining a target potential to which a capacitor in a cardiac stimulating device must be charged to allow said cardiac stimulating device to deliver a desired energy output. The capacitor has a nominal capacitance and an actual capacitance that may differ from the nominal capacitance, and is in series with a resistor having a known resistance. The method includes changing potential on the capacitor, measuring potential on one of (a) the capacitor, and (b) the resistor, while the potential on the capacitor is changing, measuring the time interval required for the potential on that one of (a) the capacitor, and (b) the resistor, to fall from a first predetermined potential to a second predetermined potential, and calculating the target potential from the first and second predetermined potentials, the time interval, the known resistance and the desired energy output.

Where the capacitor is an electrolytic capacitor requiring re-forming and the cardiac stimulating device contains a discharge resistor for that purpose, the determination of target potential can be accomplished during a re-forming cycle, resulting in no added power consumption to make the determination.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 1 is a partial schematic diagram, partially in block form, of a first embodiment of a cardiac stimulating device incorporating the present invention;

FIG. 2 is a graphic representation of the discharge curve for the capacitor shown in FIG. 1;

FIG. 3 is a representation of the contents of a sample lookup table in accordance with the present invention;

FIG. 4 is a simplified schematic representation of the high voltage generator shown in FIG. 1;

DETAILED DESCRIPTION OF THE PREFERRED EMBODIMENTS

Figure 5:
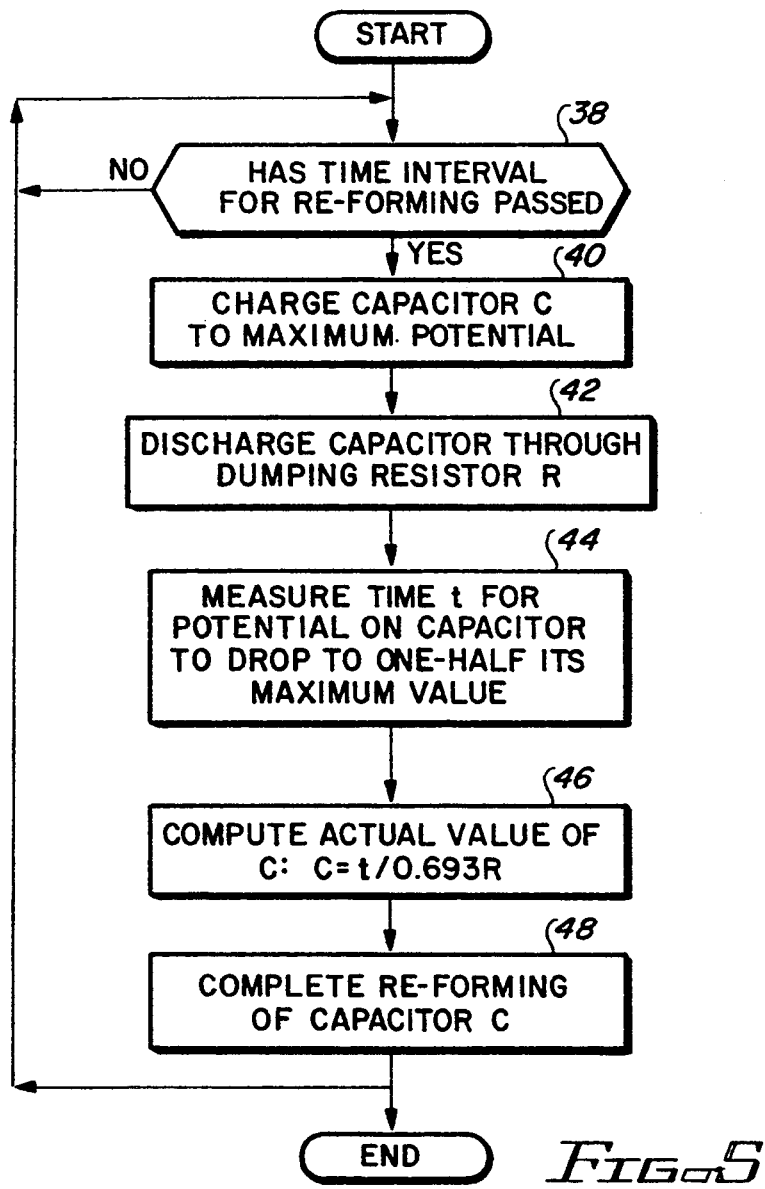
FIG. 5 is a flow diagram of a sample software routine used by the microprocessor shown in FIG. 1 to carry out the method of the present invention.

The present invention relies on the well known relationship between the resistance R and capacitance C, respectively, of a resistor and a capacitor in series—i.e., a series R-C circuit. In such a circuit, when charge on the capacitor is discharged through the resistor, the potential on the capacitor drops in accordance with the relation:

$$V(t) = V_o e^{-(t/RC)},$$

where $V_o$ is the initial potential on the capacitor, t is the discharge time, R is the resistance and C is the capacitance. It is axiomatic that if all but one of these quantities are known, the one unknown quantity can be determined; in the present invention, it is the capacitance that is unknown.

Specifically, in accordance with the present invention, the capacitor whose value is uncertain is charged to a known potential $V_o$ and then discharged. The time necessary for the potential on the capacitor to drop from $V_o$ to a predetermined fraction f—e.g., one-half—of $V_o$ is measured, and is used to calculate the true value of the capacitance C as follows:

$$\begin{aligned} V(t) &= fV_o = V_o e^{-(t/RC)} \\ f &= e^{-(t/RC)} \\ \ln f &= -(t/RC) \\ t/RC &= \ln(1/f) \\ C &= t/(R\ln(1/f)). \end{aligned} \quad (2)$$

The potential needed to store a certain energy E at a capacitance C can be derived from relation (1), above:

$$V = \sqrt{(2E/C)}. \quad (3)$$

Thus, once the capacitance has been determined from relation (2), the target potential to which the capacitor should be charged to store energy E can be determined from relation (3).

Alternatively, relation (2) and relation (3) can be combined to yield the target potential directly as a function of the time interval t required to discharge from $V_o$ to $fV_o$:

$$V = \sqrt{((2ER\ln(1/f))/t)}. \quad (4)$$

Although any fraction f can be used, in a preferred embodiment of the present invention, f = 0.5. Therefore, in the preferred embodiment:

$$C = t/R\ln 2 = t/0.693R, \text{ and} \quad (5)$$

$$V = \sqrt{(2ER\ln 2/t)} = \sqrt{(2.386RE/t)}. \quad (6)$$

A first preferred embodiment of a cardiac stimulating device circuit 10 that operates accordance with the present invention is shown in FIG. 1. Only the components necessary to the present invention are shown in FIG. 1, the remaining components being conventional and well known in cardiac stimulating devices. In particular, circuit 10 includes capacitor 12, having capacitance C, on which the energy pulse is to be stored for delivery to the patient's heart. Preferably, capacitor 12 is an electrolytic capacitor having capacitance C on the order of about 150 μF. Capacitor 12 is charged by high voltage generator 14, which as stated above may be of conventional design for a cardiac stimulating device.

Circuit 10 also includes resistor 16 having resistance R, and switch 18 which, when closed, puts resistor 16 in series with capacitor 12 for discharging capacitor 12. Resistance R of resistor 16 is preferably between about 10 kΩ and about 100 kΩ, and in any event is made (a) small enough that the current through resistor 16 during discharge of capacitor 12 is much greater than the capacitor leakage current, and (b) large enough so that resistor peak power dissipation during capacitor discharge is not excessively high (e.g., to avoid unacceptable temperature increase in the cardiac stimulating device). Resistor 16 and switch 18 would normally already be present in a conventional cardiac stimulating device of the type in which capacitor 12 is of the electrolytic type, for use in re-forming, capacitor 12. Even where re-forming is not contemplated, or in addition to being provided for re-forming, such a resistor would also be provided to allow charge to be drained from the capacitor if the remaining charge from a previous pulse exceeds the requirements for an upcoming pulse. Resistor 16 is therefore sometimes referred to as a "dumping resistor."

The present invention allows these components to be used—during the re-forming process or otherwise—to also determine the true capacitance of capacitor 12, thus allowing such a determination to be made without requiring any additional components in a device for which maintaining a small size is important. Because the method of the invention is preferably carried out during re-forming which occurs in any event, it also requires no power consumption beyond that necessary for ordinary device operation, which is important in a device for which battery replacement requires surgery and which is intended to last a lifetime.

Voltage measuring circuit 20, which measures the potential on capacitor 12 (or resistor 16) and which is also used in the re-forming process, is used in the present invention to determine when the potential on capacitor 12 (or resistor 16) has reached the predetermined potential $fV_o$ and, as a result, terminates further charging by the high voltage generator 14. The analog output of voltage measuring circuit 20 digitized by analog-to-digital converter 22 and fed to microprocessor 24, which controls circuit 10 (and all operations of the cardiac stimulating device).

Microprocessor 24 includes, either on board or as a separate circuit element, a timer 26 which can measure the time interval t as well as perform other timing functions such as determining when it is time to re-form capacitor 12. Microprocessor 24 also has associated random access memory 28, as well as a lookup table 30 whose function will be described in more detail below.

Microprocessor 24 initiates the process of the present invention at programmed intervals, as measured, e.g., by timer 26, or at intervals established by a physician when using a pacemaker programmer. As set forth above, the programmed intervals may be those at which re-forming of capacitor 12 is required. The interval should be such that the value of capacitance C would not be expected to change so much during such an interval that the previously determined value could not be used reliably in determining the energy pulse to be delivered to the patient. Microprocessor 24 instructs high voltage generator 14 to charge capacitor 12 to potential $V_o$, which might be that ordinarily used in the re-forming process. Switch 18 is then closed and timer 26 measures the time interval t until voltage measuring circuit 20 shows that the potential on capacitor 12 has fallen to $fV_o$.

FIG. 2 shows an example of a discharge curve 32 for capacitor 12, having been initially charged to a potential $V_o$. As shown, the potential on capacitor 12 falls to $0.5V_o$ after 0.693RC or 69.3% of the "time constant" of a series circuit of capacitor 12 and resistor 16 having capacitance C and resistance R respectively. After one full time constant, the potential has fallen to $0.368V_o$.

Once the desired time interval has been measured, it can be stored by microprocessor 24 in random access memory 28 for later use in relation (4) (or relation (6) where $f = 0.5$) in determining the target potential for capacitor 12 for a pulse of energy E. Alternatively, microprocessor 24 can use time interval t in conjunction with relation (2) (or relation (5) where $f = 0.5$) to determine the actual value of C, which can be stored in random access memory 28. The stored value of C can then be used by microprocessor 24 in conjunction with relation (3) in determining the target potential for capacitor 12 for a pulse of energy E.

Although microprocessor 24 can be used to actually compute the necessary target potential for capacitor 12 when called upon to deliver a pulse of energy E, using the stored value of either t or C, it may be faster to provide lookup table 30 as part of circuit 10, either as a separate component or stored in random access memory 28. Lookup table 30 may contain a matrix or table of target potentials for different energy values as a function of the stored time interval t. Alternatively, and more particularly preferred in the present invention, lookup table 30 can contain a matrix or table of target potentials for different energy values as a function of the stored value of capacitance C. Such a table is shown in FIG. 3.

As shown in FIG. 3, the nominal capacitance C of capacitor 12 is 150 $\mu F$, and target potentials for delivering energy pulses between 5 joules and 40 joules (for a defibrillator) are shown for that capacitance. Similar values may be stored for capacitances of 140 $\mu F$, 145 $\mu F$, 155 $\mu F$ and 160 $\mu F$, as shown, and for other values of C (not shown) if a greater variation is possible.

If a lookup table 30—e.g., as shown in FIG. 3—is used, microprocessor 24 would look in the row for the desired energy value and the column for the determined capacitance (or time interval) to determine the target potential for charging capacitor 12. If the determined capacitance (or time interval) is not specifically provided for in lookup table 30, microprocessor 24 can use the potential value from the column for the capacitance (or time interval) that is closest to the determined value or, if more precision is required, microprocessor 24 can interpolate between the values in the two closest columns using linear interpolation or any other suitable interpolation technique.

Alternatively, it may be possible to provide a plurality of lookup tables. One lookup table would provide the nominal potential for a desired energy pulse, while another lookup table would provide an offset potential based on the stored value of t or C as determined in accordance with the invention. Microprocessor 24 would add the offset potential from the second lookup table to the nominal potential from the first lookup table to determine the target potential.

Although the invention has thus far been described in terms of an embodiment including resistor 16, it may be implemented without resistor 16—e.g., using the internal resistance of high voltage generator 14. Such an implementation could be used where a re-forming resistor 16 is not already provided—such as in a cardiac stimulating device that does not include an electrolytic capacitor—in keeping with the object of the invention not to require additional components. As seen in FIG. 4, high voltage generator 14 can be considered schematically as a source of potential 34 and an internal resistance 36. At the moment the process of charging capacitor 12 is selected, there is no current flow in capacitor 12, and thus instantaneously there is no potential difference across resistance 36. Then, at the moment current starts to flow, a potential difference between potential source and capacitor 12 appears on resistance 36, decreasing exponentially as capacitor 12 is charged. By measuring the potential on capacitor 12 using circuit 20, and subtracting out the potential of source 34, the potential on resistance 36 can be determined. The falling potential on resistance 36 as capacitor 12 is charged can be measured just as the falling potential on capacitor 12 as it is discharged is measured in the first preferred embodiment, and the time constant, and therefore the value of capacitance C, can be determined.

A preferred embodiment of the method according to the present invention is diagrammed in FIG. 5 as it might be programmed into micro-processor 24 in suitable microcode form or in any higher level computing language. The method starts at test 38 where the system determines (e.g., based on timer 26) whether or not the predetermined time interval for re-forming the capacitor has passed. If not, the system continues to loop back to test 38. If, at test 38, the predetermined time interval for re-forming the capacitor has passed, then at step 40 the capacitor is charged to the predetermined maximum value, and at step 42 it is discharged through the dumping resistor. At step 44, the time interval for the capacitor to discharge to half the predetermined maximum value is measured, and the actual value of capacitance C is computed at step 46 from relation (5) and stored (or at step 46 the measured time interval t may simply be stored). The system then finishes the re-forming process at step 48 and loops back to test 38 to wait for the next re-forming interval. In the interim, the stored value of capacitance C (or time interval t) will be used if it becomes necessary to deliver an energy pulse to the patient.

Figure 6:
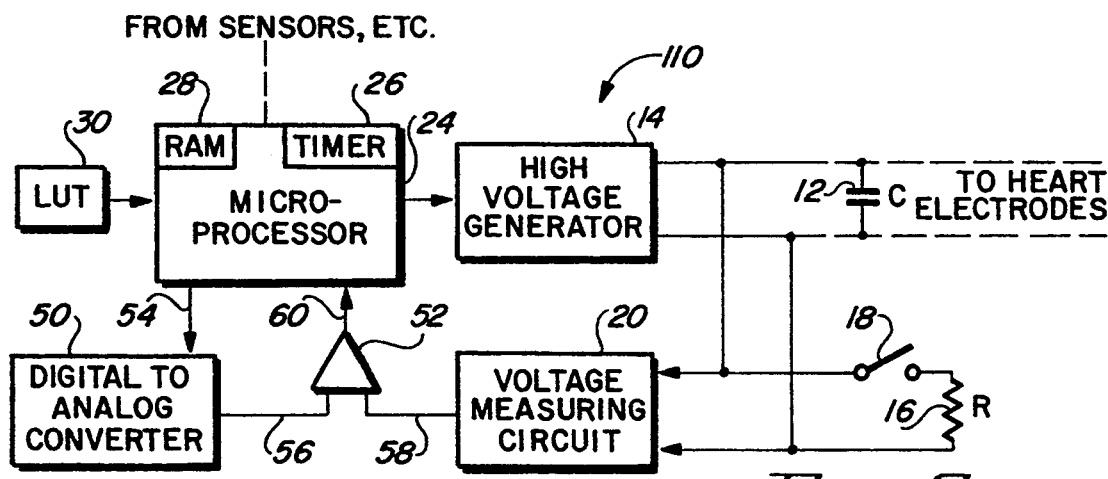
FIG. 6 is a partial schematic diagram, partially in block form, of a second preferred embodiment of a cardiac stimulating device incorporating the present invention.

A more particularly preferred embodiment of the present invention is shown in FIG. 6. Circuit 110 is similar to circuit 10, except that analog-to-digital converter 22 is replaced by digital-to-analog converter 50 and comparator 52. Circuit 110 can follow the falling potential on capacitor 12 better than circuit 10 because digital-to-analog converter 50 is faster than analog-to-digital converter 22, which might not be able to follow in real time the very rapid discharge of capacitor 12. Analog-to-digital converter 22 is still fast enough to measure the charging of capacitor 12 and may be retained in the cardiac stimulating device for other functions, including, possibly, monitoring the charging of capacitor 12, but in this embodiment it is not used in the portion of the cardiac stimulating device associated with the present invention, and so it is not shown in FIG. 6.

Circuit 110 operates like circuit 10, except that microprocessor 24 outputs the voltage value, to which the potential on capacitor 12 must fall to establish the time interval t, as a digital output at 54. Digital output 54 is converted to an analog signal 56 by digital-to-analog converter 50 and serves as one input to comparator 52. The other input to comparator 52 is the output 58 of voltage measuring circuit 20.

When it is desired to determine time interval t to calibrate the true capacitance of capacitor 12, microprocessor 24 causes capacitor 12 to be charged to a known potential $V_o$ as above. Microprocessor 24 can also immediately or shortly thereafter output the value fV$_o$, to which the potential on capacitor 12 will fall to define time interval t, as a digital signal at 54. When the actual potential V$_c$ on capacitor 12 falls to fV$_o$, comparator 52, which has V$_c$ as one input and fV$_o$ as its other input, will change state relatively rapidly. This change of state is monitored by microprocessor 24 at 60, and the determination of time interval t is made quickly on the detection of the change of state at 60. In contrast, in circuit 10, microprocessor 24 must continually monitor the output of analog-to-digital converter 22 and calculate when that output is equal to fV$_o$. In circuit 110, there is no such need to calculate, so that the change of state is detected more quickly, and in addition microprocessor resources are conserved. One skilled in the art will appreciate that there are, of course, still other ways to monitor the potential V$_c$ on capacitor 12 and rapidly detect when that potential V$_c$ reaches fV$_o$.

Thus it is seen that a method and apparatus for determining a target potential to which a capacitor in a cardiac stimulating device must be charged to allow the cardiac stimulating device to deliver a desired energy output, taking into account capacitor tolerances and variations, without using additional battery power or requiring additional components, are provided. One skilled in the art will appreciate that the present invention can be practiced by other than the described embodiments, which are presented for purposes of illustration and not of limitation, and the present invention is limited only by the claims which follow.

What is claimed is:

1. A method for determining a target potential to which a capacitor in a cardiac stimulating device must be charged to allow said cardiac stimulating device to deliver a desired energy output, wherein said capacitor has a nominal capacitance and an actual capacitance that may differ from said nominal capacitance and is in series with a resistor having a known resistance, said method comprising:
   charging the capacitor to develop a potential thereon;
   discharging the capacitor for thereby changing the potential on the capacitor as a function of time;
   measuring the potential on one of (a) the capacitor, and (b) the resistor, while said potential on the capacitor is changing;
   measuring the time interval required for said potential on said one of (a) the capacitor, and (b) the resistor, to fall from a first predetermined potential to a second predetermined potential; and
   calculating said target potential from said first and second predetermined potentials, said time interval, said known resistance and said desired energy output.

2. The method of claim 1, wherein said step of calculating said target potential comprises determining said actual capacitance from said first and second predetermined potentials, said time interval and said known resistance.

3. The method of claim 2, wherein said step of determining said actual capacitance comprises determining a time constant for a series circuit of said capacitor and said resistor from said first and second predetermined potentials and said time interval.

4. The method of claim 1, wherein said step of calculating said target potential comprises calculating said target potential from said first and second predetermined potentials, said time interval and said known resistance.

5. The method of claim 1, wherein:
   said step of changing potential on said capacitor comprises discharging said capacitor from said first predetermined potential to said second predetermined potential; and
   said step of measuring potential comprises measuring potential on said capacitor.

6. The method of claim 5, wherein said second predetermined potential is one-half of said first predetermined potential.

7. The method of claim 6, wherein said step calculating said target potential comprises calculating said target potential in accordance with the formula:

$$V_c = \sqrt{(1.386RE/t)},$$

where V$_c$ is said target potential, R is said known resistance, E is said desired energy output, and t is said time interval.

8. The method of claim 5, wherein said step of calculating said target potential comprises calculating said target potential in accordance with the formula:

$$V_c = \sqrt{[2RE\ln(x)/t]},$$

where V$_c$ is said target potential, R is said known resistance, E is said desired energy output, t is said time interval, and x is the ratio of said first predetermined potential to said second predetermined potential.

9. In a cardiac stimulating device, said cardiac stimulating device including:
   a capacitor having a nominal capacitance and an actual capacitance that may differ from said nominal capacitance,
   a power source for charging said capacitor to a target potential for delivering a desired energy output,
   a potential measuring circuit for measuring potential on said capacitor,
   a microprocessor for controlling functions of said cardiac stimulating device, and
   a resistor having a known resistance for re-forming said capacitor;
   a method for determining said target potential to which said capacitor must be charged to allow said cardiac stimulating device to deliver said desired energy output, accounting for variation between said nominal capacitance and said actual capacitance, without increasing power consumption in said cardiac stimulating device, said method comprising:
   initiating re-forming of said capacitor including:
      charging said capacitor from said power source to a first predetermined potential, and
      discharging said capacitor through said resistor;
   measuring, with said potential measuring circuit, potential on said capacitor while said capacitor is discharging through said resistor;
   measuring with said microprocessor the time interval required for said capacitor to discharge from said first predetermined potential to a second predetermined potential; and
   calculating with said microprocessor said target potential from said first and second predetermined potentials, said time interval, said known resistance and said desired energy output.

10. The method of claim 9, wherein said step of calculating said target potential comprises determining said actual capacitance from said first and second predetermined potentials, said time interval and said known resistance.

11. The method of claim 10, wherein said step of determining said actual capacitance comprises determining a time constant for a series circuit of said capacitor and said resistor from said first and second predetermined potentials and said time interval.

12. The method of claim 9, wherein said step of calculating said target potential comprises calculating said target potential from said first and second predetermined potentials, said time interval and said known resistance.

13. The method of claim 9, wherein said second predetermined potential is one-half of said first predetermined potential.

14. The method of claim 13, wherein said step of calculating said target potential comprises calculating said target potential in accordance with the formula:

$$V_c = \sqrt{(1.386RE/t)},$$

where $V_c$ is said target potential, R is said known resistance, E is said desired energy output, and t is said time interval.

15. The method of claim 9, wherein said step of calculating said target potential comprises calculating said target potential in accordance with the formula:

$$V_c = \sqrt{[2REln(x)/t]},$$

where $V_c$ is said target potential, R is said known resistance, E is said desired energy output, t is said time interval, and x is the ratio of said first predetermined potential to said second predetermined potential.

16. A cardiac stimulating device comprising:
a capacitor having a nominal capacitance and an actual capacitance that may differ from said nominal capacitance,
a power source coupled to said capacitor for charging said capacitor to a target potential for delivering a desired energy output,
a resistor having a known resistance switchably coupled to said capacitor for discharging said capacitor for re-forming said capacitor;
a potential measuring circuit coupled to said capacitor for measuring the potential on said capacitor;
a microprocessor for controlling operation of said cardiac stimulating device; and wherein:
said microprocessor initiates re-forming of said capacitor, by initiating charging of said capacitor from said power source to a first predetermined potential and discharging said capacitor through said resistor; and further wherein:
said microprocessor measures the time interval required for said capacitor to discharge from said first predetermined potential to a second predetermined potential; and still further wherein:
said microprocessor calculates said target potential from said first and second predetermined potentials, said time interval, said known resistance and said desire energy output.

17. The cardiac stimulating device of claim 16, wherein said microprocessor calculates said target potential by determining said actual capacitance from said first and second predetermined potentials, said time interval and said known resistance.

18. The cardiac stimulating device of claim 17, wherein said microprocessor determines said actual capacitance by determining a time constant for a series circuit of said capacitor and said resistor from said first and second predetermined potentials and said time interval.

19. The cardiac stimulating device of claim 16, wherein said microprocessor calculates said target potential from said first and second predetermined potentials, said time interval and said known resistance.

20. The cardiac stimulating device of claim 16, wherein said second predetermined potential is one-half of said first predetermined potential.

21. The cardiac stimulating device of claim 20, wherein said microprocessor calculates said target potential in accordance with the formula:

$$V_c = \sqrt{(1.386RE/t)},$$

where $V_c$ is said target potential, R is said known resistance, E is said desired energy output, and t is said time interval.

22. The cardiac stimulating device of claim 21, further comprising a lookup table loaded in accordance with said formula, said microprocessor calculating said target potential with reference to said lookup table.

23. The cardiac stimulating device of claim 22, wherein said microprocessor interpolates between values in said lookup table.

24. The cardiac stimulating device of claim 16, wherein said microprocessor calculates said target potential in accordance with the formula:

$$V_c = \sqrt{[2REln(x)/t]},$$

where $V_c$ is said target potential, R is said known resistance, E is said desired energy output, t is said time interval, and x is the ratio of said first predetermined potential to said second predetermined potential.

25. The cardiac stimulating device of claim 24, further comprising a lookup table loaded in accordance with said formula, said microprocessor calculating said target potential with reference to said lookup table.

26. The cardiac stimulating device of claim 25, wherein said microprocessor interpolates between values in said lookup table.

* * * * *

UNITED STATES PATENT AND TRADEMARK OFFICE
CERTIFICATE OF CORRECTION

PATENT NO. : 5,350,405
DATED : September 27, 1994
INVENTOR(S) : Sergiu Silvian

It is certified that error appears in the above-identified patent and that said Letters Patent is hereby corrected as shown below:

In col. 3, line 46, delete "2.386" and substitute therefor —1.386—.

Signed and Sealed this

Sixteenth Day of April, 1996

Attest:

BRUCE LEHMAN

Attesting Officer      Commissioner of Patents and Trademarks